United States Patent [19]
Benvegnu et al.

[11] Patent Number: 5,900,130
[45] Date of Patent: May 4, 1999

[54] METHOD FOR SAMPLE INJECTION IN MICROCHANNEL DEVICE

[75] Inventors: Dominic Benvegnu, La Honda; Randy M. McCormick, Santa Clara, both of Calif.

[73] Assignee: Alcara BioSciences, Inc., Hayward, Calif.

[21] Appl. No.: 08/878,447

[22] Filed: Jun. 18, 1997

[51] Int. Cl.$^6$ .................................................. G01N 27/26
[52] U.S. Cl. ........................... 204/453; 204/454; 204/604
[58] Field of Search ..................................... 204/451–455, 204/601–605; 422/68.1, 100, 102, 101, 70; 435/287.2, 288.5; 210/656–658, 198.2, 198.3

[56] References Cited

U.S. PATENT DOCUMENTS

| | | | |
|---|---|---|---|
| 4,908,112 | 3/1990 | Pace | 204/299 |
| 5,126,022 | 6/1992 | Soane et al. | 204/180 |
| 5,250,263 | 10/1993 | Manz | 422/81 |
| 5,599,432 | 2/1997 | Manz et al. | |
| 5,779,868 | 7/1998 | Parce et al. | |
| 5,800,690 | 9/1998 | Chow et al. | |

FOREIGN PATENT DOCUMENTS

| | | |
|---|---|---|
| 0 620 432 A1 | 10/1994 | European Pat. Off. . |
| WO 96/04547 | 2/1996 | WIPO . |

OTHER PUBLICATIONS

Harrison et al., "Capillary Electrophoresis and Sample Injection Systems Integrated on a Planar Glass Chip," *Anal. Chem*, (1992), 64, pp. 1926–1932.

Jacobson et al., "Microchip Capillary Electrophoresis with an Integrated Postcolumn Reactor," *Anal. Chem*, (1994), 66, pp. 3472–3476.

Jacobson et al., "Effects of Injection Schemes and Column Geometry on the Performance of Microchip Electrophoresis Devices," *Anal. Chem*, (1994), 66, pp. 1107–1113.

*Primary Examiner*—William H. Beisner
*Attorney, Agent, or Firm*—Flehr Hohbach Test Albritton & Herbert LLP

[57] ABSTRACT

A method and device are provided for transporting a liquid sample into a third microchannel from an intersection of at least a first, a second, and a fourth microchannel, by stages. In a first stage, liquid sample is moved in and from the fourth microchannel through the intersection and into the second microchannel and concurrently carrier liquid is moved in and from the first and third microchannels through the intersection and into the second microchannel. Thereafter in a second stage, at least part of the contents of the intersection is moved into the third channel and concurrently a part of the contents of the second and fourth microchannels is moved through the intersection and into the third microchannel. Thereafter in a third stage, carrier liquid is moved from the first microchannel simultaneously through the intersection and into the second, third, and fourth microchannels. In some embodiments the liquid sample and the carrier liquid are moved electrokinetically, that is, by application of an electric field to segments of the microchannels.

18 Claims, 4 Drawing Sheets

METHOD FOR SAMPLE INJECTION IN MICROCHANNEL DEVICE

BACKGROUND

This invention relates to microfluidic manipulations in microchannel structures.

Considerable attention has been directed to developing microchannel structures having capillary dimensions, in which small volumes of liquids and small quantities of materials carried in liquids can be transported electrokinetically, that is, under the driving force of an applied electric field. Application of an electric field to a liquid (such as a solvent) in a microchannel results both in a bulk flow of the liquid and of materials carried in it (such as solutes) owing to electroosmotic movement of the liquid, and in electromigration of the materials themselves in the liquid. Accordingly, elecromigration can be used to separate materials that have different electrophoretic mobilities in the liquid, and both electroosmotic flow and electromigration can be used to transport substances from point to point within the microchannel device.

A variety of approaches have been described for employing electroosmotic flow to carry out valveless injections of samples in microchannel devices.

D. J. Harrison et al (1992), "Capillary Electrophoresis and Sample Injection Systems Integrated on a Planar Glass Chip", *Anal. Chem.* 64:1926–32, proposes a scheme for valveless switching of fluid flow in channels intersecting at a T-junction. In this scheme, a sample supply channel, a "mobile phase" supply channel, and a separation channel meet at a common intersection point. An electrode is placed at an inlet at the head of each channel. A sample containing a mixture of fluorescent dyes is introduced by syringe into the sample supply channel, and then the mobile phase supply channel and the separation channel are flushed by syringe with buffer. Then a voltage is applied between reservoirs at the heads of the sample supply channel and the separation channel, causing the sample solution in the sample supply channel to move into and along the separation channel past a fluorescent detector. According to this scheme a plug of sample can be injected into the separation channel from the sample supply channel by applying the voltage across the sample supply reservoir and separation reservoir for a brief period, and then allowing the potential at the sample supply reservoir to "float" (that is, disconnecting it from both ground and power supply) while applying a voltage across the mobile phase supply and separation reservoirs to move the plug in the separation channel and effect the separation. In practice, some sample material may leak from the sample supply channel by diffusion or convection at the intersection point during the separation phase. This leakage can be reduced by applying a voltage across the mobile phase supply reservoir and the sample supply reservoir after the injection phase, drawing solvent back into the sample supply channel and displacing the sample away from the intersection.

A different scheme is described in S. C. Jacobsen et al. (1994a), "Effects of Injection Schemes and Column Geometry on the Performance of Microchip Electrophoresis Devices", *Anal. Chem.* 66:1107–13. In this scheme, four channels meet at a common intersection, forming an "injection cross". Thus, an analyte supply channel runs from an analyte reservoir to the injection cross, an analyte waste channel runs from the injection cross to an analyte waste reservoir, a buffer supply channel runs from a buffer reservoir to the injection cross, and a separation channel runs from the injection cross to a waste reservoir. The device is operated in a "sample loading mode" and a "separation mode". Two types of sample introduction are described for the sample loading mode. In a "floating" type of sample loading, a voltage is applied to the analyte reservoir with the analyte waste reservoir grounded, and with the buffer and waste reservoirs floating. As sample is drawn from the sample reservoir through the injection cross and into the sample waste channel, some sample moves laterally into the buffer supply channel and the waste channel. In a "pinched" type of sample loading, a voltage is applied to the analyte, buffer and waste reservoirs with the analyte waste reservoir grounded. As sample is drawn through the intersection the sample stream is constrained by streams of buffer entering from the buffer and waste reservoirs. After either pinched or floating sample loading, the device is switched to the separation mode. Here, a voltage is applied to the buffer reservoir with the waste reservoir grounded. To achieve a clean break of the injection plug, which is said to be mandatory to avoid tailing, buffer is drawn from the buffer channel into the analyte, analyte waste, and separator channels simultaneously, by holding the voltage at the intersection below the potential of the buffer reservoir and above the potential of the other three reservoirs, displacing the sample in the sample supply and sample waste channels away from the intersection.

A "gated valve" injection scheme employing an injection cross is described in S. C. Jacobsen et al. (1994b), "Microchip Capillary Electrophoresis with an Integrated Postcolumn Reactor", *Anal. Chem.* 66:3472–76. Here, a voltage is continuously applied to the analyte reservoir with the analyte waste reservoir grounded, so that sample is continuously drawn from the analyte reservoir to the intersection and then laterally from the intersection to the analyte waste reservoir. Simultaneously a voltage is applied to the buffer reservoir with the waste reservoir grounded, to deflect the analyte stream and prevent the sample from migrating into the separation channel. To allow the sample to migrate from the analyte supply channel across the intersection into the separation channel, the potentials at the buffer and analyte waste reservoirs are floated for a short period of time. To separate a plug of sample as it passes into the separation channel, the voltage at the buffer and analyte waste reservoir are reapplied.

Similar schemes, and variations on them, are described in International Patent Publication WO 96/04547.

Published European Patent Application EP 0 620 432 describes an "offset T" microchannel configuration for sample loading. Here supply and drain channels open by way of respective supply and drain ports into an electrolyte channel. The distance between the supply and drain ports along the electrolyte channel defines a fixed sample volume. The sample is loaded by applying a voltage across the supply and drain channels for a time at least long enough that the sample component having the lowest electrophoretic mobility is contained within the geometrically defined sample volume. Then a voltage is applied along the electrolyte channel to move the sample plug and separate the sample. Preferably, after sample loading and prior to separation, electrolyte buffer is allowed to advance into the supply channel and the drain channel from the electrolyte channel, pushing sample back into those channels and away from the sample plug in the electrolyte channel.

SUMMARY OF THE INVENTION

In one general aspect, the invention features a method for transporting a liquid sample into a third microchannel from an intersection of at least a first, a second, and a fourth microchannel, by stages. In a first stage, liquid sample is moved in and from the fourth microchannel through the intersection and into the second microchannel and concurrently carrier liquid is moved in and from the first and third microchannels through the intersection and into the second microchannel. Thereafter in a second stage, at least part of the contents of the intersection is moved into the third channel and concurrently a part of the contents of the second and fourth microchannels is moved through the intersection and into the third microchannel. Thereafter in a third stage, carrier liquid is moved from the first microchannel simultaneously through the intersection and into the second, third, and fourth microchannels.

In some embodiments at least a part of the contents of the first microchannel is additionally moved through the intersection during at least a part of the duration of the second stage.

In some embodiments the liquid sample and the carrier liquid are moved electrokinetically, that is, by application of an electric field to segments of the microchannels. The electric field can induce bulk movement of liquid contents of the microchannel by electroosmosis; and the electric field can induce electrophoretic movement of charged materials, including small ions and charged sample materials, within the contents of the microchannel. Accordingly, movement of liquid, as that term is used herein, contemplates bulk flow of liquid within the microchannel, or flow of charged materials within the contents of the microchannel, or combinations of bulk flow of liquid and flow of charged materials. The rate of movement of the liquid carrier and liquid sample by electroosmosis, and the rate of movement of charged materials by electrophoresis, can be adjusted in each microchannel segment by adjusting the strength of the electric field in the segment, that is, by adjusting the potential difference at electrodes situated in contact with the microchannel contents at the ends of the respective microchannel segments.

Usually reservoirs are provided in liquid communication with the ends of the microchannels opposite the intersection, so that the respective sample liquid, or liquid carrier, or waste liquids can move between the reservoirs and the respective microchannels. In some embodiments electrodes are provided at the reservoirs in contact with fluid in the reservoirs, for applying the different electrical potentials and, accordingly, establishing the different electrical fields in the respective microchannel segments at the various stages.

The invention provides for transport of precisely metered samples over a range of sizes with high reproducibility.

DETAILED DESCRIPTION

Figure 1A:
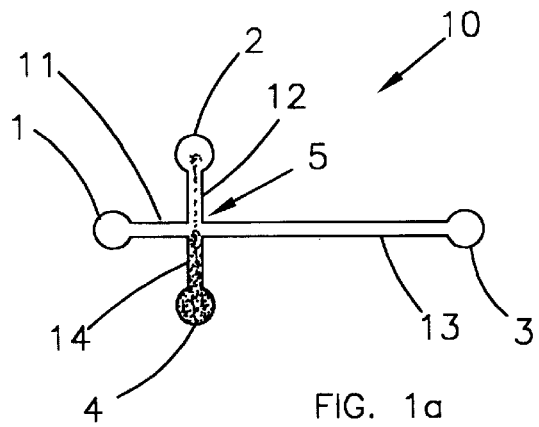
FIGS. 1a, 2a, 3a, 4a are diagrammatic sketches of a microchannel configuration in plan view illustrating steps in an embodiment of a method for sample injection according to the invention.

Referring now to FIG. 1a, there is shown generally at 10 a simple microchannel system having reservoirs 1, 2, 3, 4 in fluid communication with channels 11, 12, 13, 14, which meet at a common intersection or injection cross, shown generally at 5. Thus the injection cross is connected to buffer reservoir 1 by way of buffer supply channel 11, to sample reservoir 4 by way of sample supply channel 14, to sample waste reservoir 2 by way of sample waste channel 12, and to waste reservoir 3 by way of separation channel 13. Each of reservoirs 1, 2, 3, 4 has associated with it an electrode (not shown in the Figs.) connected to a power supply (not shown) by way of means for manually and/or automatically controlling the electrical potential at each electrode.

The microchannel system is prepared for use by filling the reservoirs and the channels with a liquid carrier medium such as a buffer, and sample reservoir 4 is filled with a liquid in which a material of interest is carried.

Figure 1B:
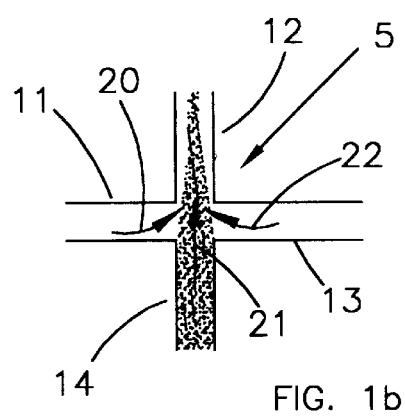
FIGS. 1b, 2b, 3b, 4b are diagrammatic sketches showing the injection cross of FIGS. 1a, 2a, 3a, 4a in greater detail.

In a first stage of sample injection according to the invention, illustrated in progress in FIGS. 1a and 1b, the electrical potentials at the reservoirs are adjusted so that liquid containing the material of interest flows from sample reservoir 4 through sample supply channel 14 into injection cross 5, and then across injection cross 5 into sample waste channel 12 toward sample waste reservoir 2; and so that, concurrently, liquid carrier medium flows from buffer reservoir 1 through buffer supply channel 11 to injection cross 5 and then into sample waste channel 12 and from waste reservoir 3 through separation channel 13 to injection cross 5 and then into sample waste channel 12. This flow pattern can be achieved, for example, by raising the electric potential at sample waste reservoir 2 above that in the other three reservoirs, so that fluid is drawn electrokinetically toward waste reservoir 2 from the other three sources.

As appears more clearly in FIG. 1b, during this first phase the flow of liquid containing the material of interest (indicated in FIG. 1b by arrow 21) is constrained at the intersection of the channels by the flow of carrier fluid entering the intersection on one side (indicated in FIG. 1b by arrow 20) from the buffer supply channel and on the other side (indicated in FIG. 1b by arrow 22) from the separation channel.

Figure 2A:
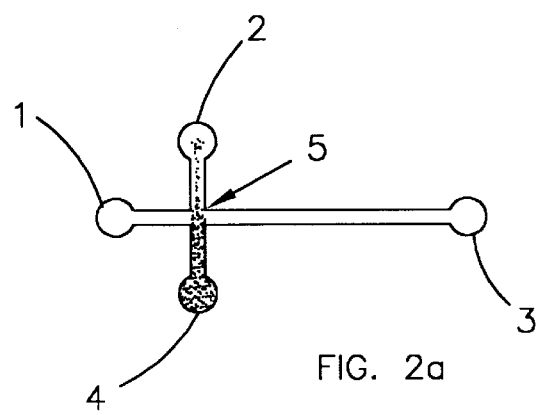
Figure 2B:
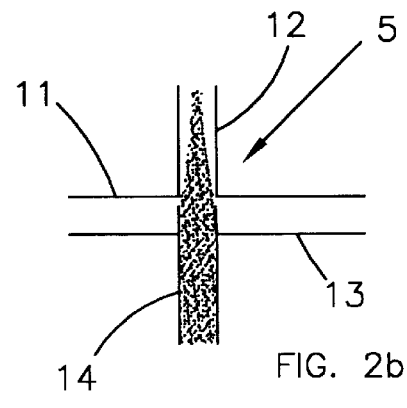

Then the flows in all the channels are momentarily stopped, as illustrated in FIGS. 2a and 2b. At this point liquid containing the material of interest occupies sample supply channel 14, much of the intersection of the channels, and some of at least that part of sample waste channel 12 that is near the intersection. The flows can be stopped, for example, by adjusting the potentials so that they are the same in all four reservoirs.

Figure 3A:
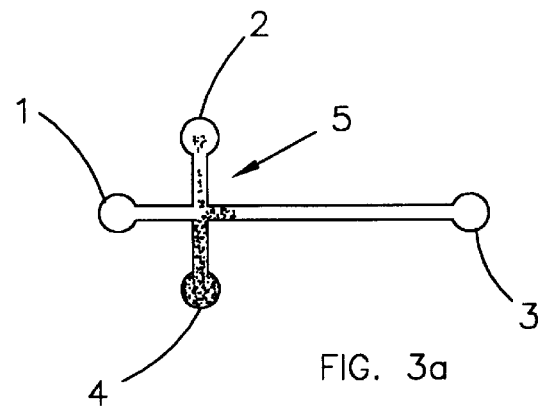
Figure 3B:
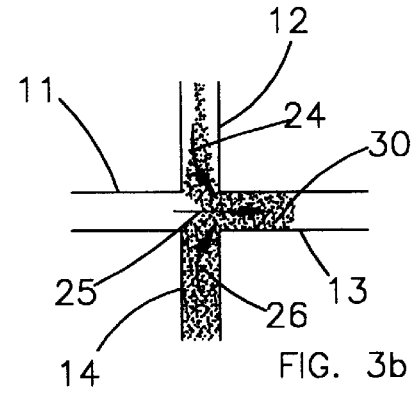

Then, in a second phase, illustrated in progress in FIGS. 3a and 3b, the electrical potentials at the reservoirs are adjusted so that fluid flows into the separation channel 13 from the intersection itself, as well as from the parts of the channels 11, 12, and 14 that are near the intersection. This flow can be achieved, for example, by raising the electrical potential at the waste reservoir above that at the other three reservoirs, so that fluid is drawn electrokinetically toward waste reservoir 2 from the other three sources.

As appears more clearly in FIG. 3b, during this second phase a plug 30 of liquid containing the material of interest begins to form and to move in separation channel 13 toward waste reservoir 3, supplied from the sample supply channel 14 (as indicated by arrow 26) and from the sample waste channel 12 (as indicated by arrow 24), and followed behind by movement of carrier medium from the buffer supply channel 11 (as indicated by arrow 25). This second phase is maintained for a selected period of time, during which the plug 30 continues to form as it moves toward waste reservoir 3.

Figure 4A:
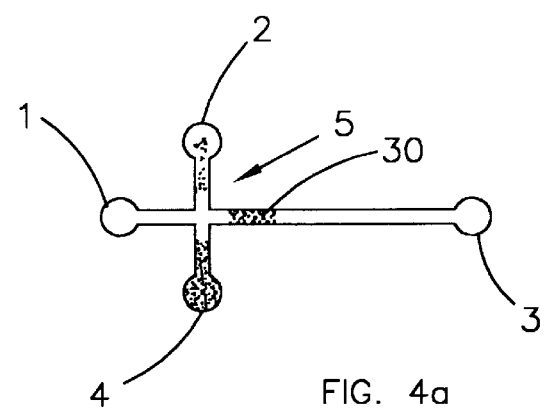
Figure 4B:
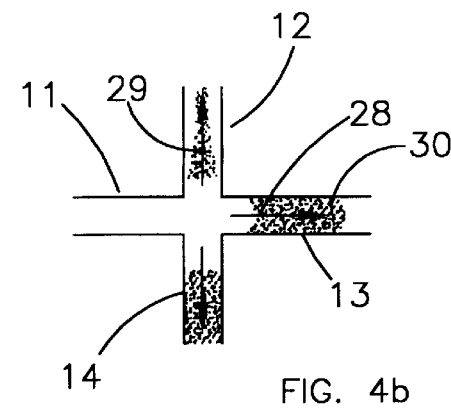

In a third phase, shown in progress in FIGS. 4a and 4b, the electrical potentials at the reservoirs are adjusted so that carrier medium moves into the intersection and into sample waste channel 12 and sample supply channel 14 and separation channel 13, while fluid containing the material of interest is drawn back away from the intersection in sample supply channel 14 toward sample reservoir 4 and in sample waste channel 12 toward sample waste reservoir 2 and so that the plug 30, now constituting the injected sample, moves in separation channel 13 toward waste reservoir 3.

The flow pattern in the injection cross appears more clearly in FIG. 4b, where the movement of the plug 30 is indicated by arrow 28, and movement of liquid containing the material of interest away from the intersection in sample supply channel 14 and in sample waste channel 12 is indicated by arrows 27 and 29, respectively.

As will be apparent, to the extent the sample contains a mixture of components having differing electrophoretic mobilities, the components will become separated as they move in the electric field within the separation channel. A suitable detector arranged at a downstream point along the separation channel can be used to detect the components as they pass.

Microchannel systems according to the invention can be constructed from any of a variety of materials using any of a variety of techniques. Preferred devices are made by forming an open channel pattern having the desired configuration and dimensions in a planar surface of a substrate material, and then enclosing the channels by covering the surface with a planar cover material. Techniques of photolithography and wet etching have been employed to create microchannels in silicon or glass or quartz substrates, as described for example in D. J. Harrison et al .(1992), S. C. Jacobsen el al. (1994a), S. C. Jacobsen et al. (1994b), WO 96/04547, and EP 0 620 432, supra, and in U.S. Pat. No. 4,908,112 and U.S. Pat. No. 5,250,263. Examples of techniques for fabricating microchannel systems from plastic materials are described in U.S. patent application Ser. No. 08/853,661, filed May 9, 1997.

Figure 9:
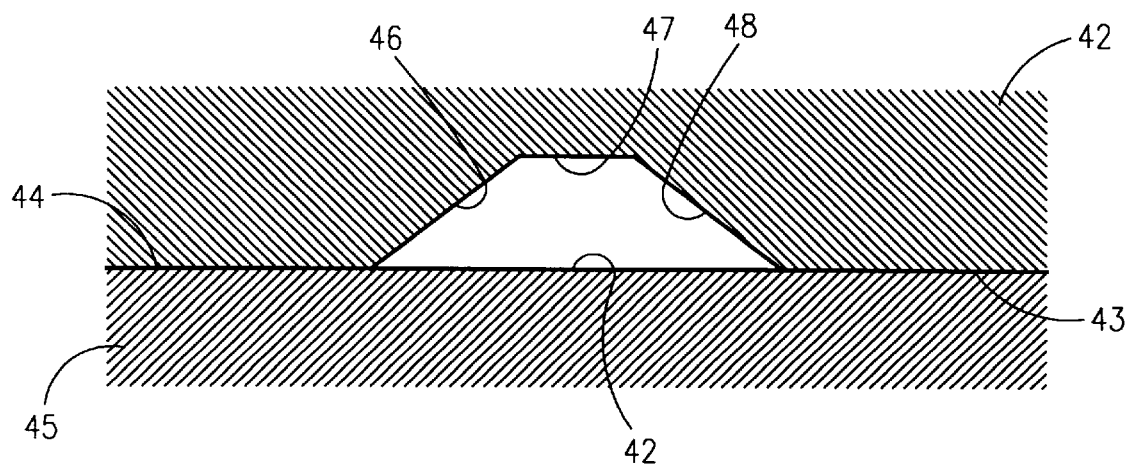
FIG. 9 is a diagrammatic sketch in sectional view of a portion of a microchannel device constructed as described in Example 1, showing a microchannel in transverse section.

FIG. 9 shows a portion of a microchannel device in sectional view passing transversely through a channel, for illustration. A base plate 42 has a channel 40 formed in a generally planar surface 43. A cover 45 has a generally planar surface 42, which is apposed to the surface 43 of the base plate to enclose the channel 40. Where the base plate is fabricated by injection molding, for example, using techniques of photolithography and wet etching to construct the mold in one or a series of steps, the resulting channel has a roughly trapezoidal cross-sectional shape. Walls 46, 47, and 48 are formed in the base plate material and enclosing wall 42 is constituted from a portion of the surface 44 of the cover 45. Suitable techniques for bonding the surfaces 43 and 44 are disclosed in U.S. patent application Ser. No. 08/853,661, filed May 9, 1997. Reservoirs can be formed for example by providing holes through the cover material at appropriate points.

Suitable techniques for placing electrodes at desired points in the device are disclosed for example in U.S. Pat. No. 5,126,002 and in U.S. patent application Ser. No. 08/853,661, filed May 9, 1997. The electrode includes a conductive material in contact with fluid in the reservoir or in the channel at the desired point. The conductive material is preferably an electrochemically inert material such as, for example, platinum or palladium or carbon. The electrode can be laid down as a trace on the base plate or on the cover, by a technique such as, for example, electroplating or vapor deposition.

EXAMPLES

The following Examples illustrate fabrication and of microchannel devices having a microchannel configuration generally as described in FIGS. 1a,b through 4a,b, and operation of the devices according to the invention.

Example 1

In this Example a microchannel device having a microchannel configuration generally as sketched in FIGS. 1a,b through 4a,b is constructed by forming a base plate and cover of acrylic polymer, and the apposing surfaces are bonded together by a thermobonding technique.

Briefly, photolithographic, electroforming and injection molding techniques were used to prepare an acrylic polymer (AtoHaas, Plexiglas™V825NA-100) microchannel base plate. The microchannel structure corresponds to two crossed linear channels of dimensions 2 cm and 5.5 cm in length respectively. The channel has a trapezoidal cross-section, measuring at widest about 120 $\mu$m and at narrowest about 50 $\mu$m, with an average depth about 50 $\mu$m. At the termini of the channels, holes of 3 mm in diameter were drilled as buffer reservoirs.

A flat acrylic polymer plate, injection molded using similar techniques, was used as a cover to enclose the microchannel structure. Physical bonding between the base and cover plates was achieved using a thermobonding procedure carried out generally as follows. The microchannel base plate and the flat cover plate were mounted together in a mechanical fixture that allows plate heating and mechanical encasing of the two plates under pressure. For bonding, the fixture containing the microchannel cassette structure was heated to 104° C. at a rate of 1° C./min in an oven. The temperature was then maintained 104° C. for 2 hours. During this time, the two plate surfaces melted and fused to each other. To complete the bonding, the temperature was reduced to room temperature at a rate of 1° C./min. Then the fixture was opened and the acrylic/acrylic microchannel structure was removed.

In the resulting microchannel containing cassettes, the channels are limited by four acrylic walls produced from the same acrylic injection molding resin. In cross-section the channels were roughly trapezoidal, about 50 $\mu$m in depth (d in FIG. 9), about 50 $\mu$m wide in the narrower dimension (w in FIG. 9) and about 120 $\mu$m wide in the wider dimension (w' in FIG. 9).

Electrodes of 76 micron diameter platinum wire were routed to each of the four reservoirs and terminated at one edge of the chip with a 4-prong 2.54 mm pitch KK® electrical heater (Waldon Electronics).

Example 2

In this Example a microchannel device having a microchannel configuration generally as sketched in FIGS. 1a,b through 4a,b is constructed by forming a base plate of acrylic polymer, and thermally laminating a Mylar™ sheet by a thermally activated adhesive.

Briefly, an acrylic polymer base plate was formed generally as described in Example 1, and the channels were covered by thermal lamination of a 2 mil thick sheet of Mylar™ coated with a thermally-activated adhesive (MonoKote™, made by Top Flight Co.) at 105° C. for 5 minutes.

The separation microchannel formed this way has three acrylic limiting walls (46, 47, 48 in FIG. 9) and a fourth wall surface of the MonoKote™ adhesive (42 in FIG. 9). In cross-section the channels were about 50 μm in depth (d in FIG. 9), about 50 μm wide in the narrower dimension (w in FIG. 9) and about 120 μm wide in the wider dimension (w' in FIG. 9).

As in Example 1, electrodes of 76 micron diameter platinum wire were routed to each of the four reservoirs and terminated at one edge of the chip with a 4-prong 2.54 mm pitch KK® electrical heater (Waldon Electronics).

Example 3

This Example illustrates operation of a device made as in Example 1 or Example 2, according to the invention.

The assembled device was loaded with buffer by filling reservoirs 1, 2, and 4 with buffer and then applying a vacuum at reservoir 3 to draw the buffer into the channels 11, 12, 13, 14; then reservoir 3 was filled with buffer. Then, buffer was removed from sample supply reservoir 4, and replaced with buffer containing the sample material.

Then voltages were applied in stages as illustrated in FIGS. 5–8.

Figure 5:
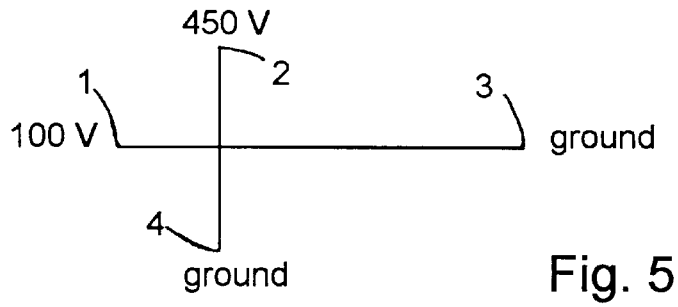
FIGS. 5–8 are diagrammatic sketches showing voltage parameters suitable for carrying out a sample injection according to the invention in a device constructed as described in Example 1.

Particularly, in a first stage, illustrated in FIG. 5, the electrode at sample supply reservoir 4 was grounded, and a potential of 450 V was applied to the electrode at sample waste reservoir 2. At the same time, the electrode at waste reservoir 3 was grounded and a potential of 100 V was applied to the electrode at buffer supply reservoir 1. This resulted in a pattern of fluid movement through the injection cross generally as described above with reference to FIGS. 1a,b. Accordingly, as a result of the potential differences between the sample supply reservoir and the sample waste reservoir, sample material flows through the sample supply channel across the intersection into the sample waste channel; and, at the same time, as a result of the potential differences between the waste reservoir and the sample waste reservoir, and between the buffer supply reservoir and the waste reservoir, buffer is drawn into the intersection and then into the sample waste channel on either side of the flow of sample material.

Figure 6:
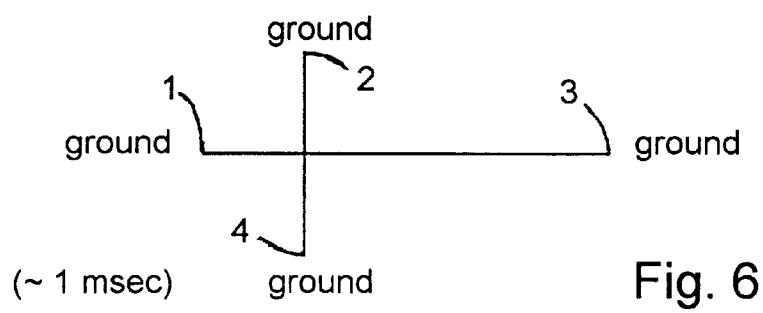

Once the constrained flow of sample material into the sample waste channel is established, completing the first stage, the movement is momentarily stopped, as illustrated in FIGS. 2a,b by grounding all four electrodes for about 1 msec, as illustrated in FIG. 6.

Figure 7:
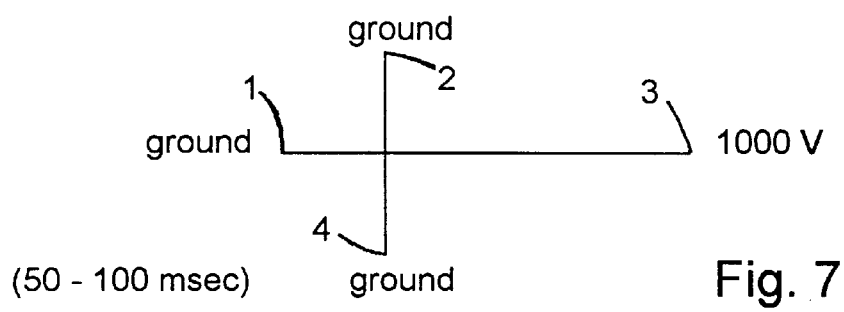

Then, in a second stage, illustrated in FIG. 7, a relatively high potential (1000 V in this Example) is applied to the electrode at the waste reservoir 3, and the other four reservoirs 1, 2, and 4 are grounded. This stage is maintained for a period of time t; as described more fully below increasing the time t increases the size of the sample plug, as well as the quantitative reproducibility of the sample material in the plug. This results in a flow pattern in the injection cross generally as described with reference to FIGS. 3a,b. Accordingly, the potential difference between the electrode at the waste reservoir and the other reservoirs draws fluid from the sample supply channel, the sample waste channel and the buffer supply channel into the intersection, beginning the formation of the sample plug 30 in the separation channel 13.

Figure 8:
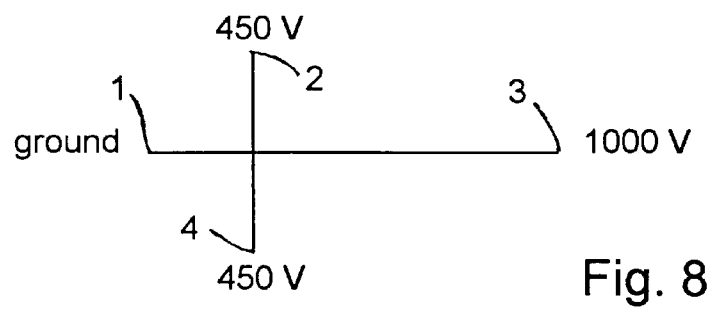

Then in a third stage, illustrated in FIG. 8, the electrode at waste reservoir 3 is kept at a relatively high voltage (1000 V in this Example) and the electrode at the buffer supply reservoir 1 is kept at ground, and at the same time the electrodes at the sample supply and sample waste reservoirs 2, 4 are raised to an intermediate potential (450 V in this Example). This results in a flow pattern in the injection cross generally as described with reference to FIGS. 4a,b. Thus, the potential difference between the electrode at the waste reservoir and the electrode at the buffer supply reservoir draws buffer through the buffer supply channel across the intersection into the separation channel, following the sample plug in its movement toward the waste reservoir; and at the same time, the potential difference between the electrodes at the sample supply reservoir and the buffer supply reservoir, and between the electrodes at the sample waste reservoir and the buffer supply reservoir, draw buffer through the intersection and into the sample supply and sample waste channels, causing the sample material there to be drawn away from the intersection and from the moving plug.

As will be appreciated, the potential differences required to provide the flow patterns in the different stages will be different for different channel configurations and dimensions.

Example 4

Generally, the longer the potential differences are maintained in the second stage, producing the flow pattern illustrated in FIGS. 3a,b, the greater the quantity of sample material in the plug, and the better the quantitative reproducibility of the sample material in the plug. This example illustrates the effect on the size of the sample plug of varying the length of time t that a system described as in Example 1 is held in the second stage. In this Example, the carrier liquid is 0.5×TBE buffer (49.5 millimolar tris, 49.5 millimolar boric acid, 1 millimolar EDTA, pH 8.3), and the sample material is fluorescein, at a concentration about 100 micromoles in the sample supply reservoir. The fluorescein sample plug was detected fluorometrically downstream in the separation channel.

Figure 10:
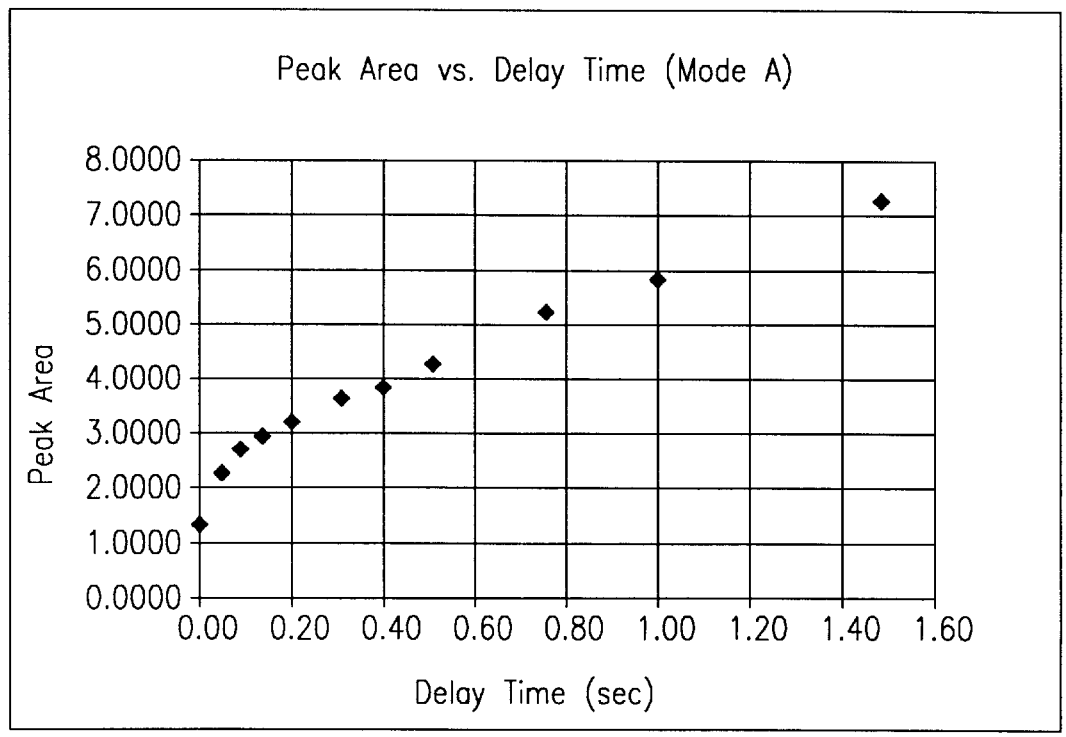
FIG. 10 is a plot of data for sample injection using a device as illustrated in FIGS. 1a,b through 4a,b, comparing sample profiles resulting from a method according to the invention in which the step shown in FIGS. 3a,b is carried out for various time periods (t=0.10, 0.20, 0.50, and 1.00 sec.), and from a method omitting the step shown in FIGS. 3a,b (t=0 sec.).

The results are plotted in FIG. 10. The "delay time" is the length of time t that the system is held at the second stage.

Example 5

This Example further illustrates the effect on the size of the sample plug of varying the length of time t that the system described in Example 1 is held in the second stage.

Figure 11:
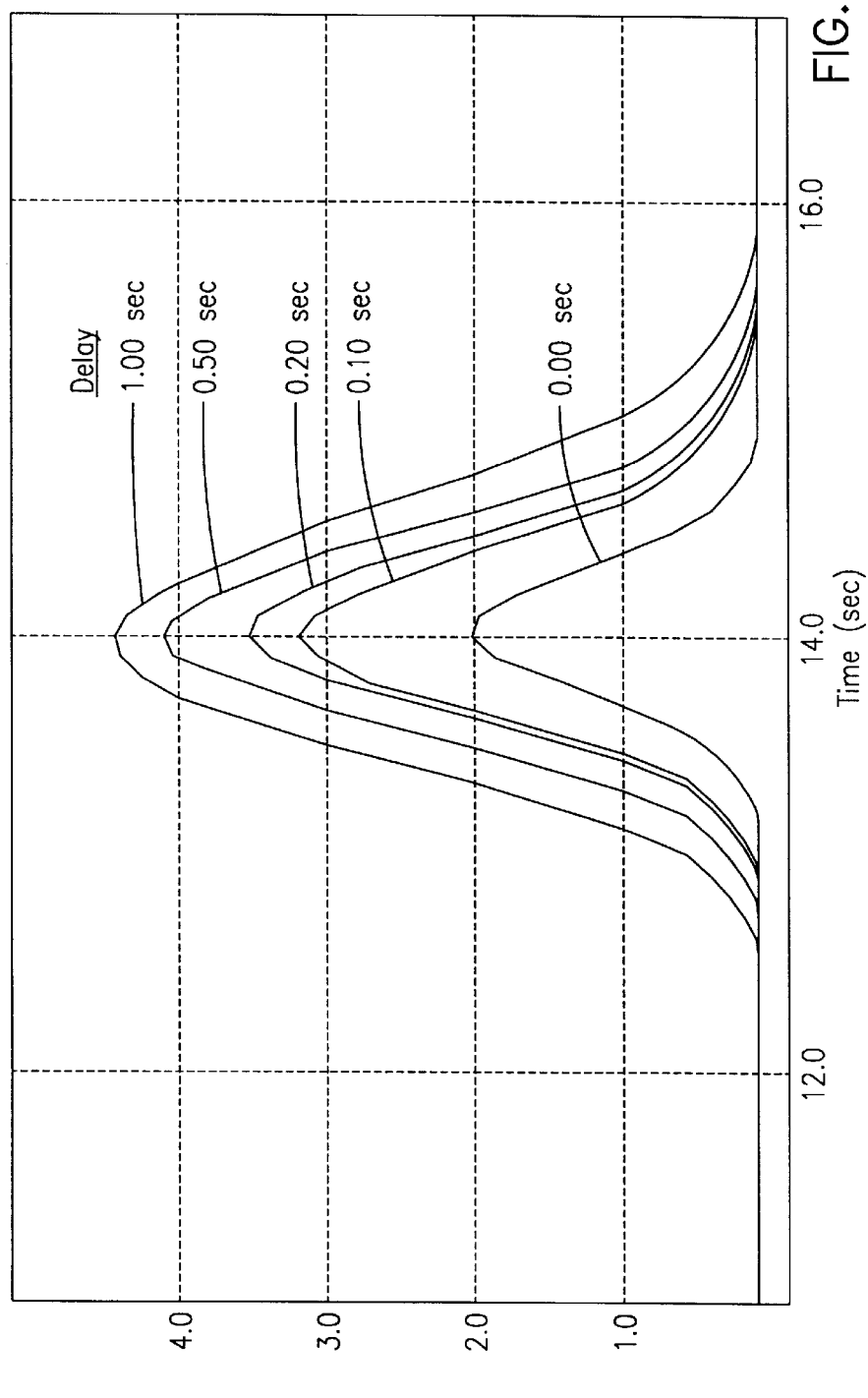
FIG. 11 is a plot of data for sample injection using a device as illustrated in FIGS. 1a,b through 4a,b, comparing sample profiles resulting from a method according to the invention in which the step shown in FIGS. 3a,b is carried out for various time periods (t=0.05, 0.10, 0.15, 0.20, 0.30, 0.40, 0.50, 0.75, 1.00 and 1.50 sec.), and from a method omitting the step shown in FIGS. 3a,b (t=0 sec.).

The system was operated as described in Example 4. The results are plotted in FIG. 11. Here, the intensity of fluorescence detected at the detector as the sample plug passes is plotted for samples resulting from a regime in which there is no second stage (t=0) and in which the second stage is maintained for various periods.

Example 6

This Example illustrates improved reproducibility resulting from increasing the time t during which a system made as in Example 1 ["Acrylic Cover"] and as in Example 2 ["MonoKote™ Cover"] is operated according to the invention, and maintained in the second stage for various times t.

The results are shown in Table 1.

TABLE I

Sample Reproducibility

| t (sec) | Acrylic cover Sample Peak Area RsD (n = 5) | MonoKote ™ cover Sample Peak Area RsD (n = 5) |
|---|---|---|
| .050 | 1.57% | 4.94% |
| .100 | 1.26% | 1.45% |
| .200 | 1.10% | 1.04% |
| .500 | 0.64% | — |

OTHER EMBODIMENTS

Other embodiments are within the claims.

For example, other geometrical arrangement of the channels at the intersection may be used, and more than four microchannels may be in fluid communication with the intersection. For example, the intersection need not form a cross of two pairs of aligned microchannels, and the respective microchannels need not intersect at right angles, as shown in the Figs. The channels need not all intersect at a mutual point; the intersection may itself constitute a microchannel segment, so that an offset T configuration results.

And, for example, as noted in the summary of the invention, fluid need not be drawn through the intersection from the buffer supply channel during the second stage; instead, the potential at the buffer supply reservoir may be allowed to float during the second stage, or adjusted to some fixed or variable intermediate potential (rather than at ground, as shown in the Figs.), so that substantially no carrier liquid moves into the intersection, at least during the earlier part of the second stage.

As will be appreciated, the rate and timing of movement of the contents of the various segments of the microchannels at the various stages can be controlled with considerable precision by adjusting and changing the magnitudes of the electrical potentials at the respective electrodes. To a good approximation, substantially no movement of liquid from a reservoir through a microchannel segment into the intersection will result whenever the electrical field strength between the reservoir and the intersection is approximately zero; and a more rapid movement through the segment will result from a higher potential difference. The potentials required to produce the desired resultant flows in the various segments can accordingly be estimated by treating the microchannel structure as an arrangement of interconnected electrical resistors, and applying principles of electrical circuit analysis to the system. To a reasonable approximation, for example, for a microchannel segment of a given cross-section dimension and containing a given liquid carrier, the electrical resistance is proportional to the length of the segment.

In some embodiments the contents of the microchannels have a relatively low viscosity, so that application of an electrical potential to a microchannel segment results in both bulk flow by electroosmosis and electromigration of charged particles within the liquid by electrophoresis. Bulk flow phenomena may predominate, for example, where the channels are filled with buffer at the outset, and where the liquid carrier and sample liquid are buffer solutions. In other embodiments the microchannels (or at least some of them) can be filled with an electrophoretic medium that has sieving properties; such media characteristically have a higher viscosity, and where such media are employed, the extent of bulk flow resulting from application of an electrical potential is reduced. The microchannels may be charged at the outset with a viscous polymer, for example, or with an electrophoretic gel medium such as a polyacrylamide or an agarose, and in such instances the extent of flow of charged materials by electrophoresis predominates, and there may be substantially no bulk flow. Or, the surfaces of the microchannel walls may be fabricated of a material that is characterized by reduced electroosmotic flow, such as for example an electrically neutral polymer or plastic. Here, too, the extent of bulk flow may be substantially reduced.

It is evident from the above results and discussion that improved methods for transporting materials in microchannel structures are provided.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A method for transporting a liquid sample containing at least one sample material into a third microchannel from an intersection of said third microchannel with at least a first, a second, and a fourth microchannel, comprising:

in a first stage, moving liquid sample in and from said fourth microchannel through said intersection and into said second microchannel and concurrently moving carrier liquid in and from said first microchannel and in and from said third microchannel through said intersection and into said second microchannel; thereafter in a second stage, moving at least part of the contents of said intersection into said third microchannel and concurrently moving a part of the contents of said second and fourth microchannels through said intersection and into said third microchannel, whereby a quantity of said sample material is moved into said third microchannel; and thereafter in a third stage, moving carrier liquid from said first microchannel simultaneously through said intersection and into said second, third, and fourth microchannels.

2. The method of claim 1 wherein the second stage is maintained for a time t, and whereby the magnitude of said quantity of liquid sample moved into said third channel is greater for greater t.

3. The method of claim 2 wherein t is at least about 0.01 seconds.

4. The method of claim 1 wherein said moving in each said stage is induced by establishing an electrical field within the liquid contents of at least a segment of at least one of said microchannels.

5. The method of claim 4 wherein a reservoir is provided in fluid communication with an end of each said microchannel opposite said intersection, and said electric field is established by applying an electrical potential difference between at least two electrodes in contact with fluid in at least two of said reservoirs.

6. The method of claim 5 wherein the rate of said moving in each said stage is determined by the magnitude of said electric potential.

7. The method of claim 4 wherein establishment of said electric field in the liquid contents of said microchannel segment induces an electroosmotic flow of said fluid in said microchannel segment, resulting in bulk movement of said liquid contents within said microchannel.

8. The method of claim 4 wherein establishment of said electric field in the liquid contents of said microchannel segment induces an electroosmotic flow of said fluid in said microchannel segment, resulting in bulk movement of said liquid contents within said microchannel, and induces an electrophoretic migration of said sample material within said microchannel.

9. The method of claim 4 wherein establishment of said electric field in the contents of said microchannel segment induces an electrophoretic migration of said sample material within said microchannel.

10. A method for transporting a liquid sample containing at least one sample material into a third microchannel from an intersection of said third microchannel with at least a first, a second, and a fourth microchannel, comprising:

in a first stage, moving liquid sample in and from said fourth microchannel through said intersection and into said second microchannel and concurrently moving carrier liquid in and from said first microchannel and in and from said third microchannel through said intersection and into said second microchannel; thereafter in a second stage, moving at least part of the contents of said intersection into said third microchannel and concurrently moving a part of the contents of said second, fourth and first microchannels through said intersection and into said third microchannel, whereby a quantity of said sample material is moved into said third microchannel; and thereafter in a third stage, moving carrier liquid from said first microchannel simultaneously through said intersection and into said second, third, and fourth microchannels.

11. The method of claim 10 wherein the second stage is maintained for a time t, and whereby the magnitude of said quantity of liquid sample moved into said third channel is greater for greater t.

12. The method of claim 11 wherein t is at least about 0.01 seconds.

13. The method of claim 10 wherein said moving in each said stage is induced by establishing an electrical field within the liquid contents of at least a segment of at least one of said microchannels.

14. The method of claim 13 wherein a reservoir is provided in fluid communication with an end of each said microchannel opposite said intersection, and said electric field is established by applying an electrical potential difference between at least two electrodes in contact with fluid in at least two of said reservoirs.

15. The method of claim 14 wherein the rate of said moving in each said stage is determined by the magnitude of said electric potential.

16. The method of claim 13 wherein establishment of said electric field in the liquid contents of said microchannel segment induces an electroosmotic flow of said fluid in said microchannel segment, resulting in bulk movement of said liquid contents within said microchannel.

17. The method of claim 13 wherein establishment of said electric field in the liquid contents of said microchannel segment induces an electroosmotic flow of said fluid in said microchannel segment, resulting in bulk movement of said liquid contents within said microchannel, and induces an electrophoretic migration of said sample material within said microchannel.

18. The method of claim 13 wherein establishment of said electric field in the contents of said microchannel segment induces an electrophoretic migration of said sample material within said microchannel.

* * * * *

UNITED STATES PATENT AND TRADEMARK OFFICE
CERTIFICATE OF CORRECTION

PATENT NO. : 5,900,130
DATED : May 4, 1999
INVENTOR(S): Dominic Benvegnu and Randy M. McCormick.
TITLE : METHOD FOR SAMPLE INJECTION IN MICROCHANNEL DEVICE

It is certified that error appears in the above-identified patent and that said Letters Patent is hereby corrected as shown below:

Title page, [73], "Alcara" should read --ACLARA--.

Signed and Sealed this

Eleventh Day of January, 2000

Attest:

Q. TODD DICKINSON

*Attesting Officer*    *Acting Commissioner of Patents and Trademarks*